(12) United States Patent
Sung et al.

(10) Patent No.: US 9,095,605 B2
(45) Date of Patent: Aug. 4, 2015

(54) COMPOSITION FOR PREVENTING VIRUS INFECTION COMPRISING POLY-GAMMA-GLUTAMIC ACID

(75) Inventors: Moon-Hee Sung, Daejeon (KR); Chul Joong Kim, Daejeon (KR); Haryoung Poo, Daejeon (KR); Young-Ki Choi, Chungcheongbuk-do (KR); Il Han Lee, Gyeonggi-do (KR); Dai-Won Yoo, Daejeon (KR)

(73) Assignees: BIOLEADERS CORPORATION (KR); KOREA RESEARCH INSTITUTE OF BIOSCIENCE AND BIOTECHNOLOGY (KR)

( * ) Notice: Subject to any disclaimer, the term of this patent is extended or adjusted under 35 U.S.C. 154(b) by 205 days.

(21) Appl. No.: 13/234,670

(22) Filed: Sep. 16, 2011

(65) Prior Publication Data

US 2012/0010130 A1 Jan. 12, 2012

Related U.S. Application Data

(63) Continuation of application No. 12/678,027, filed as application No. PCT/KR2007/004419 on Sep. 13, 2007.

(51) Int. Cl.
*A61K 38/16* (2006.01)
*A61K 31/785* (2006.01)

(52) U.S. Cl.
CPC ............. *A61K 31/785* (2013.01); *A61K 38/164* (2013.01)

(58) Field of Classification Search
CPC . A61K 31/685; A61K 31/785; A61K 38/164; C07K 14/32
See application file for complete search history.

(56) References Cited

U.S. PATENT DOCUMENTS

| 4,140,762 | A * | 2/1979 | Bachmayer et al. ....... 424/210.1 |
| 7,582,466 | B2 | 9/2009 | Sung et al. |
| 2006/0127447 | A1 | 6/2006 | Sung et al. |
| 2006/0134143 | A1* | 6/2006 | Schneerson et al. ....... 424/246.1 |
| 2009/0092633 | A1 | 4/2009 | Akashi et al. |
| 2009/0285901 | A1 | 11/2009 | Akashi et al. |
| 2010/0256050 | A1 | 10/2010 | Sung et al. |

FOREIGN PATENT DOCUMENTS

| CN | 1665862 A | 9/2005 |
| KR | 100475406 B1 | 2/2005 |
| KR | 100496606 B1 | 6/2005 |
| KR | 100500796 B1 | 7/2005 |
| WO | 2004007593 A1 | 1/2004 |
| WO | 2006090968 A1 | 8/2006 |
| WO | WO/2006/090968 * | 8/2006 |
| WO | 2006112477 A1 | 10/2006 |

OTHER PUBLICATIONS

Firbas et al. ("Immunogenicity and safety of a novel therapeutic hepatitis C virus (HCV) peptide vaccine: A randomized, placebo controlled trial for dose optimization in 128 healthy subjects," Vaccine, 2006, 24, 4343-4353).*
Canine Parvovirus—The Merck Veterinary Manual, 2011, Merck Sharp & Dohme Corp., a subsidiary of Merck & Co., Inc. Whitehouse Station, NJ USA.*
Seong et al. Machine translation of KR 100496606, downloaded from http://kposd.kipo.go.kr on Mar. 30, 2015.*
Canadian Office Action, Sep. 26, 2011.
Chinese Office Action, Jun. 6, 2014.

\* cited by examiner

*Primary Examiner* — Christina Bradley
(74) *Attorney, Agent, or Firm* — Tristan A. Fuierer; Moore & Van Allen, PLLC

(57) ABSTRACT

The present invention relates to a pharmaceutical composition for inhibiting or preventing viral infection, which comprises an effective dose of poly-gamma-glutamic acid (γ-PGA), and more particularly, to a pharmaceutical composition, a functional food, and a feedstuff additive capable of inhibiting viral infection and preventing viral diseases, which comprise poly-gamma-glutamic acid having an infection-inhibiting effect against viruses, such as an influenza virus, inducing respiratory infection or systemic infection, as an effective ingredient.

The composition containing poly-gamma-glutamic acid as an effective ingredient according to the present invention, is effective for use as an animal feedstuff additive or a pharmaceutical agent for preventing influenza virus infection and various viral diseases as well as a pharmaceutical composition and a functional food to promote human health.

9 Claims, 3 Drawing Sheets

COMPOSITION FOR PREVENTING VIRUS INFECTION COMPRISING POLY-GAMMA-GLUTAMIC ACID

CROSS-REFERENCE TO RELATED APPLICATIONS

This application is a continuation of U.S. patent application Ser. No. 12/678,027, filed on May 7, 2010, entitled "COMPOSITION FOR PREVENTING VIRUS INFECTION COMPRISING POLY-GAMMA-GLUTAMIC ACID" in the name of Moon-Hee Sung, which claims the benefit of International Patent Application No. PCT/KR2007/004419, filed on Sep. 13, 2007, all of which are hereby incorporated by reference herein in their entirety.

TECHNICAL FIELD

The present invention relates to a pharmaceutical composition for inhibiting or preventing viral infection, which comprises an effective dose of poly-gamma-glutamic acid, and more particularly, to a pharmaceutical composition, a functional food, and a feedstuff additive capable of inhibiting viral infection and preventing viral diseases, which comprise poly-gamma-glutamic acid having an infection-inhibiting effect against viruses, such as an influenza virus, inducing respiratory infection or systemic infection, as an effective ingredient.

BACKGROUND ART

Influenza virus belongs to the Orthomyxoviridae family, and has 8 RNA fragments, PB2, PB1, PA, HA, NP, NA, M and NS. It is basically composed of a virus envelope having lipid bilayer structure, and an interior nucleocapsid surrounded by external glycoprotein or RNA combined with nucleoprotein. The internal layer of a virus envelope is mainly composed of matrix proteins, and the external layer thereof is composed of lipid materials mostly derived from a host. Among them, two proteins constituting a coat protein, i.e., hemagglutinin (hereinafter referred to as HA) and neuraminidase (hereinafter referred to as NA) are important immunogens in inducing immune antibodies, and they are characterized by being transformed through the process of antigenic shift and drift. Since this transformation of an influenza virus enables the virus to avoid the immune system against other influenza virus of the same subtypes, and generally, immunity induced by an influenza virus only lasts for a short period of time and thus immunity should be induced against a predicted pandemic virus every time. Influenzas are divided into three groups A, B, and C.

An influenza virus induces a bad cold which is an acute respiratory disease, and symptoms thereof are shown after latent period of 1~5 days. Infected people show no symptom in the beginning, but later, they show symptoms such as fever, chill, ache, anorexia and the like. In some cases, it causes viral pneumonia, bacterial pneumonia and the like, which can lead to death. During the past 250 years, there were at least 10 major influenza pandemics, and influenza epidemics caused by type A virus occur at an interval of 2~3 years. Since flu (influenza) is a viral infection of the respiratory system, it is highly contagious and has a high ratio of inapparent infection so that many people are infected at one time. It frequently occurs in children of 5~9 years old and in old people of more than 55 years old, and usually breaks out the most between fall and spring. Since it is hard to control influenza infections and most of the influenza infections are inapparent infections, it is not necessary to isolate patients. An influenza vaccine, which is an inactivated vaccine mixed with various vaccines, has some side effects and lasts only for 3~6 months, so that children and old people, who are highly susceptible to influenza, should be vaccinated yearly against flu.

Poly-gamma-glutamic acid (γ-PGA) is a mucous polymer produced by microorganisms. Specifically, PGA is produced from the genus *Bacillus* strain isolated from *Chungkookjang* (Korean traditional fermented soybean food prepared using rice-straw), *Natto* (Japanese traditional fermented soybean food), *Kinema* (fermented soybean food prepared in Nepal), etc. γ-PGA produced from the genus *Bacillus* strain is an edible, water-soluble, anionic and biodegradable polymer substance, which can be used as a raw material for humectants, moisturizers and cosmetics. Recently, studies on the use of γ-PGA in developing materials substituting for non-degradable polymers and heat-resistant plastics by esterification, and producing water-soluble fibers and membranes, are being actively performed in developed countries.

Meanwhile, the present inventors obtained a patent relating to a method for producing γ-PGA using a halophilic *Bacillus subtilis* var. *chungkookjang* that produces γ-PGA with high molecular weight (Korean Patent Registration No. 500,796). Also, they obtained patents relating to an anticancer composition, an immune adjuvant and an immune enhancing agent, which contain γ-PGA (Korean Patent Registration Nos. 496,606; 517,114; and 475,406).

Accordingly, the present inventors have made extensive efforts to develop a foodstuff additive, a functional food, and a pharmaceutical composition, which have no side effects, is not harmful to the human body and have an infection-inhibiting effect against viruses, such as influenza, inducing respiratory infection or systemic infection, and, as a result, found that viral infection could be inhibited when a livestock, to which γ-PGA is administered, was exposed to viral infection, thereby completing the present invention.

SUMMARY OF THE INVENTION

Therefore, it is a main object of the present invention to provide a pharmaceutical composition, a functional food, and a feedstuff additive capable of inhibiting viral infection to prevent diseases, which comprise poly-gamma-glutamic acid (γ-PGA) having an infection-inhibiting effect against viruses, such as an influenza virus, inducing respiratory infection or systemic infection, as an effective ingredient.

To achieve the above object, the present invention provides a pharmaceutical composition for inhibiting viral infection or preventing viral diseases, which comprises an effective dose of poly-gamma-glutamic acid.

In addition, the present invention provides a functional food for inhibiting viral infection or preventing viral diseases, which comprises an effective dose of poly-gamma-glutamic acid.

Also, the present invention provides a feedstuff additive for inhibiting viral infection or preventing viral diseases, which comprises an effective dose of poly-gamma-glutamic acid.

The above and other objects, features and embodiments of the present invention will be more clearly understood from the following detailed description and accompanying claims.

DETAILED DESCRIPTION OF THE INVENTION, AND PREFERRED EMBODIMENTS

Figure 1:
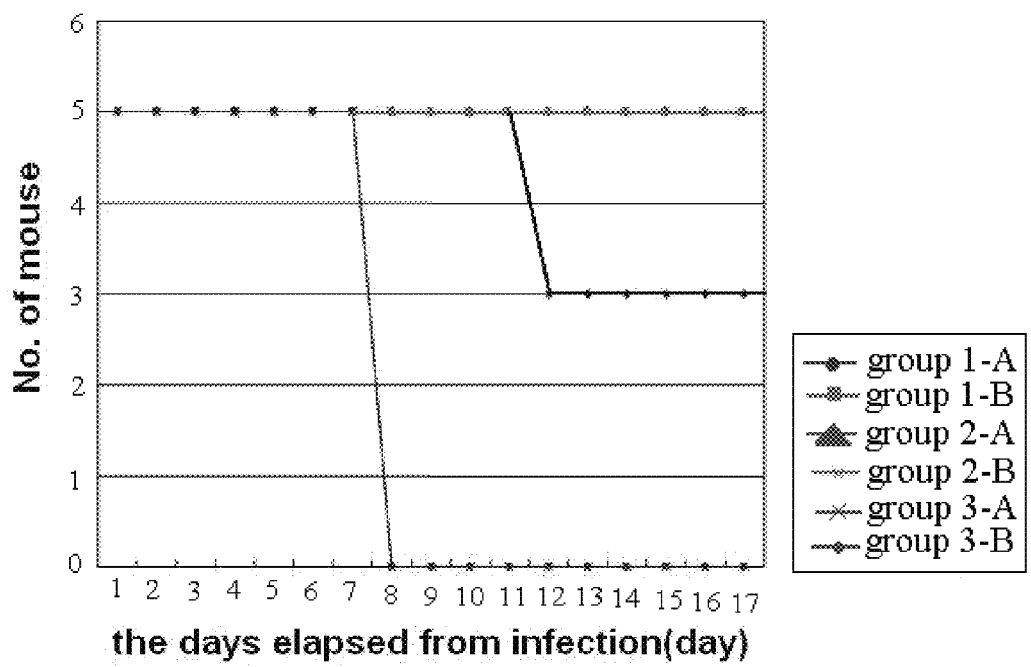
FIG. 1 is a graph showing changes in the number of infected mice survived according to the days elapsed from infection.

In one aspect, the present invention relates to a pharmaceutical composition for inhibiting viral infection or preventing viral diseases, which comprises an effective dose of poly-gamma-glutamic acid.

In the present invention, as the poly-gamma-glutamic acid having an infection-inhibiting effect and a disease preventing effect, it is preferable to use poly-gamma-glutamic acid having a molecular weight of 10 kDa~15,000 kDa, and more preferably poly-gamma-glutamic acid having a high molecular weight of 3,000 kDa~15,000 kDa In the present invention, the virus may be a virus capable of inducing respiratory infection or systemic infection, and the virus is preferably an influenza virus.

The inventive pharmaceutical composition for inhibiting viral infection and preventing viral disease can be used to prevent a pandemic influenza, the flu, a cold, throat infection, bronchitis, or pneumonia, caused by the influenza virus.

It is preferable to contain 0.2~2 parts by weight of γ-PGA based on 100 parts by weight of the inventive pharmaceutical composition for inhibiting virus infection, and in the case where the γ-PGA content is less than 0.2 parts by weight, a virus infection-inhibiting effect cannot be anticipated and in the case where the γ-PGA content is more than 2 parts by weight, an increase of an infection-inhibiting effect according to content increase cannot be anticipated as well as it causes a high cost and thus it is not economically efficient.

In case of preparing a composition comprising 0.1~2.0 parts by weight of γ-PGA in the form of liquid formulation containing ethanol, it is possible to prepare a dispersive formulation which can be used for spraying individual animals including human or large scale disinfection. In the case where ethanol content used for the dispersive formulation is more than 50%, the poly-gamma-glutamic acid may be precipitated, and in the case of less than 1%, the viscosity increases so that dispersion may not occur, thus it is preferable to add ethanol at a concentration of 1~50%.

In another aspect, the present invention relates to a functional food for preventing viral infection, which comprises an effective dose of poly-gamma-glutamic acid.

The inventive functional food may be in the form of a powder, a granule, a tablet, a capsule, or a drink, and may contain flavor ingredients, natural carbohydrates, vitamins, minerals, fragrances, colorants, extenders, stabilizers, antiseptics, and the like.

In still another aspect, the present invention relates to a feedstuff additive for preventing viral infection, which comprises an effective dose of poly-gamma-glutamic acid.

The inventive feedstuff additive can effectively prevent livestock infectious diseases, and can be fed to mammals such as cow, pig, rabbit, horse, goat, dog, cat, deer and the like, and fowl such as chicken, duck, turkey, quail and the like.

It is preferable to contain 0.2~2 parts by weight of γ-PGA based on 100 parts by weight of the inventive feedstuff additive, and in the case where the PGA content is less than 0.2 parts by weight, a virus preventing effect cannot be anticipated and in the case where the γ-PGA content is more than 2 parts by weight, an increase of an infection-inhibiting effect according to content increase cannot be anticipated, which causes economic inefficiency due to high costs thereof.

EXAMPLES

Hereinafter, the present invention will be described in more detail by examples. It is to be understood, however, that these examples are for illustrative purpose only and are not construed to limit the scope of the present invention.

Example 1

Production of γ-PGA Having Ultra High Molecular Weight and Measurement of Molecular Weight Thereof A 5 L fermenter containing a 3 L basal medium for γ-PGA production (GS medium containing 5% L-glutamic acid: 5% glucose, 1% $(NH_4)_2SO_4$, 0.27% $KH_2PO_4$, 0.42% $Na_2HPO_4.12H_2O$, 0.05% NaCl, 0.3% $MgSO_4.7H_2O$, pH 6.8) was inoculated with 1% culture broth of *Bacillus subtilis* var *chungkookjang* (KCTC 0697BP) and then cultured at a stirring speed of 150 rpm, an air injection rate of 1 vvm and a temperature of 37° C. for 72 hours. Cells were removed from the culture broth after completion of the culture using a filter press, thus obtaining a γ-PGA-containing sample solution.

2N sulfuric acid solution was added to the γ-PGA-containing sample solution and left to stand at 10° C. for 12 hours to collect a γ-PGA precipitate. The collected precipitate was washed with a sufficient amount of distilled water to obtain γ-PGA using a Nutsche filter. The obtained γ-PGA was measured for molecular weight using GPC (gel permeation column), and as a result, it was confirmed that γ-PGA having a molecular weight of 1~15,000 kDa was produced, and then separated according to molecular weight to collect γ-PGA having an average molecular weight of 7,000 kDa. The collected γ-PGA was used in the following examples.

Example 2

Toxicity Test Results Upon Oral Administration of γ-PGA

In order to examine the safety upon oral administration of γ-PGA, toxicity test upon a single oral administration of poly-gamma-glutamic acid using rats was performed by Biotoxtech Co., Ltd., an institute approved by GLP (Good Laboratory Practice) in accordance with Biotoxtech Standard Operating Procedures (SOPs), Good Laboratory Practice (GLP) regulations and test guideline.

Ten, 6-week-old male rats (159.76~199.27 g) and 10 female rats (121.60~138.80 g) were used, and the dose of γ-PGA administered to individual rats was calculated on the basis of body weight measured on the day of administration after fasting. All rats were fasted for about 16 hours but had free access to drinking water before administration, and then they were subjected to forceful oral administration with a single dose of γ-PGA by stomach tube using a disposable syringe (5 ml) having a catheter for oral administration attached thereto, followed by being fed a feedstuff 4 hours after administration.

As a preliminary experiment, 100 mg/ml of γ-PGA was orally administered to 2 male rats and 2 female rats, respectively with a single dose of 20 ml/kg, and as a result, no dead rats were observed and thus 2000 mg/20 ml/kg was used as a single dose. An expedient was administered to a control group at the same dose as that of the experimental group to which a test material is administered. The dosage to be administered was set to 20 ml/kg.

As a result, as shown in Table 1, death and general symptoms caused by oral administration of γ-PGA were not observed during the observation period. During the observation period, it was seen that the body weight of male and female rats increased in the control group and the experimental group to which a test material is administered. Autopsy results did not reveal any abnormal findings visible to the naked eye in male and female rats of the control group and the experimental group to which a test material is administered. From the result of a single oral administration of γ-PGA to rats, general symptoms and death caused by the test material were not observed so that it was determined that the fatal dose of γ-PGA was more than 2000 mg/kg in female and male rats.

$CO_2$ incubator for 1 hour. 0.1% TPCK (N-alpha-tosyl-L-phenylalanyl chloromethyl ketone) treated-trypsin EDTA not containing FBS and an alpha-MEM medium containing P/S were added to each well to culture in a cell culture incubator. After 24 hours of incubation, the cell culture plate was washed with PBS and fixed using 0.1% noble agar containing medium.

The cultured plaques were inoculated into a 24 well plate, in which the prepared MDCK cells were cultured, at a density of one plaque per well, and 0.1% TPCK treated-trypsin EDTA not containing FBS and an alpha-MEM medium containing P/S were added to each well to culture in a cell incubator. After 48 hours of incubation, media collected from each well were centrifuged, and supernatant was infected in a MDCK cell-containing flask prepared by the same method as described above to culture 36~48 hours, and then the resulting culture broth was centrifuged, followed by transferring the resulting supernatant to a micro tube to store in a low temperature freezer (−80° C.) until use for animal experiments.

TABLE 1

| Sex | Group/Dose (mg/kg) | No. of animals | 1 | 2 | 3 | 4 | 5 | 6 | 7 | 8 | 9 | 10 | 11 | 12 | 13 | 14 | 15 | Mortality (dead/total) | Approximate lethal dose (mg/kg) |
|---|---|---|---|---|---|---|---|---|---|---|---|---|---|---|---|---|---|---|---|
| | | | | | | | | Day after treatment | | | | | | | | | | | |
| Male | G1 0 | 5 | 0 | 0 | 0 | 0 | 0 | 0 | 0 | 0 | 0 | 0 | 0 | 0 | 0 | 0 | 0 | 0% (0/5) | >2000 |
| | G2 2000 | 5 | 0 | 0 | 0 | 0 | 0 | 0 | 0 | 0 | 0 | 0 | 0 | 0 | 0 | 0 | 0 | 0% (0/5) | |
| Female | G1 0 | 5 | 0 | 0 | 0 | 0 | 0 | 0 | 0 | 0 | 0 | 0 | 0 | 0 | 0 | 0 | 0 | 0% (0/5) | >2000 |
| | G2 2000 | 5 | 0 | 0 | 0 | 0 | 0 | 0 | 0 | 0 | 0 | 0 | 0 | 0 | 0 | 0 | 0 | 0% (0/5) | |

Example 3

Immune Enhancement Effect 1 of γ-PGA Against Influenza Virus

In the present example, in order to examine an infection-inhibiting effect of poly-gamma-glutamic acid specific to avian influenza virus, the animal's death, virus proliferation, and antibody production in experimental animals infected with influenza virus, were analyzed.

(1) Preparation of Virus

As influenza virus used as a pathogen, H1N1 high pathogenicity influenza virus strain (A/Puerto Rico/8/34(H1N1)) was isolated from a mouse which was donated by Prof. Choi, Young-Ki of microbiological laboratory, College of Medicine, Chungbuk National University to amplify in Madin-Darby canine kidney (MDCK) cells to use, and 6-week-old female Balb/C mice were used as experimental animals.

Isolation of pure virus was carried out as follows.

Firstly, the isolated virus was diluted in antibiotic-containing PBS to inoculate into 10-day-old embryonated white laying hen's eggs, and then subjected to a stationary culture at 37° C. for 48 hours, from which the allantonic fluid was harvested and amplified virus was used.

Secondly, MDCK cells grown in an alpha-MEM (minimum essential medium, Gibco, USA) medium containing penicillin and streptomycin, and 5% fetal bovine serum (FBS) in a 6 well cell culture plate, were washed 3 times with PBS and diluted with a medium in which penicillin and streptomycin (hereinafter referred to as P/S) were contained and FBS was not contained, and then diluted virus was added to each well to infect cells, followed by culturing in a 37° C., 5%

(2) Animal Experiments

Firstly, as a control group, mice, to which influenza virus alone was intranasally administered, was used. In an experimental group 1, poly-gamma-glutamic acid (γ-PGA) was administered to enhance immunity against virus, and then influenza virus was administered the next day, thus inhibiting viral infection. Specifically, in the experimental group 1, mice were anesthetized using diethyl ether for 30 seconds, and then, 30 µl γ-PGA (7,000 kDa) having a final concentration of 0.5% was administered to the nasal cavity of each mouse. The next day, influenza virus was simultaneously administered to the mice together with the same amount of γ-PGA.

As an experimental group 2, mice, to which γ-PGA and influenza virus were simultaneously administered on the day when the experimental group 1 was infected with virus, was used. Constitution of the experimental groups are shown in Table 2.

TABLE 2

Constitution of the experimental groups

| | Day of administration (γ-PGA or Virus) | | |
|---|---|---|---|
| Group | 1 day before administration | 0 day (D-day) | Head |
| 1 | γ-PGA | γ-PGA + Virus volume A | 5 |
| | γ-PGA | γ-PGA + Virus volume B | 5 |
| 2 | — | γ-PGA + Virus volume A | 5 |
| | — | γ-PGA + Virus volume B | 5 |
| Control group | — | Virus volume A | 5 |
| | — | Virus volume B | 5 |

Virus volume A: $2.5 \times 10^5$ $EID_{50}$,
Virus volume B: $1.25 \times 10^5$ $EID_{50}$ For viral infection, the experimental animals were anesthetized using diethyl ether for 30 seconds to intranasally administer 30 µl of virus to each mouse, and in the groups administered volume A of virus, $2.5\times10^5$ EID$_{50}$ of virus was administered and in the groups administered volume B of virus, $1.25\times10^5$ EID$_{50}$ of virus was administered.

As a result, as shown in FIG. 1, in the control group, all mice died on the 7th day after virus administration. In the experimental group to which γ-PGA and virus were simultaneously administered, 2 mice died on the 12th day after administration in the group administered volume A of virus. In experimental group 1 to which γ-PGA was administered one day before viral infection, mice survived more than 2 weeks after virus administration. It suggests that pre-administration of γ-PGA induces immunity to inhibit viral infection, as well as simultaneous administration helps each individual mouse to survive.

1 week after intranasal administration of virus, one mouse per group was euthanized at an interval of 3 days (on the 7th day, on the 10th day, and on the 13th day after virus administration) to harvest lung tissue and serum.

Titers of influenza virus in lung tissue of mice according to dates and each group were measured by the following HA (Haemagglutination) test.

Lung tissue harvested from the dead mice and mice on the corresponding days, which are anesthetized using diethyl ether for 30 seconds, by opening thoracic cavity by a midline incision, was rapidly frozen in liquid nitrogen and stored at −80° C. until assayed for titers. The harvested lung tissue was immersed in PBS (500 µl) containing antibiotics and crushed with small metallic beads sterilized with steam of high-pressure and high-humidity for 3 minutes in a tissue homogenizer. The crushed tissue was centrifuged to obtain supernatant and diluted by log 10 dilution, and then the diluted solution was inoculated into 10-day-old embryonated eggs of white laying hens.

The inoculated embryonated eggs were cultured at 37° C. for 48 hours to harvest the allantoic fluid. 50 µl of the harvested allantoic fluid was added to the first well of a round-bottom 96 well plate, and next each well was log 2 diluted in the same volume of PBS, and then 50 µl PBS was discarded after dilution of the last well. Lastly, 50 µl of PBS containing 0.5% chicken erythrocytes, was added to each well and allowed to react for 40 minutes at room temperature.

Each titer is the value calculated from log 10 dilution of inoculum solution (200 µl). N value is expressed as a logarithmic value ($\log_{10} N=10^N$).

TABLE 3

Titers of influenza virus in lung tissue of mice

| Group | Inoculum volume | Titers measured at various days elapsed from infection | | |
|---|---|---|---|---|
| | | the 7th day | the 10th day | the 13th day |
| 1 | A | 5 | — | — |
| | B | 5 | 3 | 1 |
| 2 | A | 3 | — | — |
| | B | 3 | 4 | 3 |
| 3 | A | 5.3 | x | x |
| | B | 5 | x | x |

Titer is the value calculated from log 10 dilution of inoculum solution (200 µl). N value is expressed as a logarithmic value ($\log_{10} N=10^N$).

As a result, as shown in Table 3, in the control group, the group administered volume A of virus showed a titer of 5.3, and the group administered volume B of virus showed a titer of 5, and an increase or decrease in the titer was not shown since all mice died. In the experimental group 1, the group administered volume B of virus showed a gradual decrease in titer with the passage of time. However, the titer was decreased a little in the experimental group 2. As a result, it was suggested that administration of γ-PGA helps an individual mouse overcome infectious disease caused by highly pathogenic virus. In addition, titer decrease was higher in the group immunized with γ-PGA 1 day before virus administration, suggesting that immunization with γ-PGA induces resistance against virus.

Antibody titers in sera of mice according to dates and each group were measured by the following HI (Haemagglutination Inhibition) test.

All sera were treated with RDE (receptor-destroying enzyme) extracted from *Vibrio cholerae* with a volume ratio of 1:3 (for example, adding 30 µl RDE to 10 µl serum), to culture for 18~20 hours in a culture incubator at 37° C. 25 µl of each sample, from which non-specific activities of receptors in serum were inactivated, was serially diluted (log 2) in a round-bottom 96 well plate. Second, the same volume of 4HAU virus was added to serum samples and allowed to react for 30 minutes in an incubator at 37° C. Finally, 50 µl of PBS containing 0.5% chicken erythrocyte and allowed to react at room temperature for 40 minutes.

TABLE 4

Titers of antibodies in mouse serum

| Group | Inoculum volume | Titers measured at various days elapsed from infection | | | |
|---|---|---|---|---|---|
| | | the 7th day | the 10th day | the 13th day | the 15th day |
| 1 | A | 0 | 0 | 0 | 5 |
| | B | 0 | 0 | 0 | 3 |
| 2 | A | 0 | 0 | 5 | 6 |
| | B | 0 | 0 | 2 | 3 |
| 3 | A | 0 | 0 | 0 | 0 |
| | B | 0 | 0 | 0 | 0 |

Titer is the value calculated from log 10 dilution of inoculum solution (200 µl). N value is expressed as a logarithmic value ($\log_{10} N=10^N$)

As a result, as shown in Table 4, the antibody titer against virus increased in the experimental group to which virus and γ-PGA were simultaneously administered. In the experimental group 2, antibodies started to appear on the 13th day after administration, and increased until the 15th day. In the experimental group 1, antibodies started to appear on the 15th day. In the control group, since all mice died on the 7th day, only the titer in specimens was measured and antibodies against virus were not shown. In the group immunized with γ-PGA the day before virus administration, antibodies were produced relatively late compared to the experimental group 2, but the experimental group 1 showed higher antibody production than that of the group to which γ-PGA and virus were simultaneously administered.

From this results, it was confirmed that the γ-PGA according to the present invention had an immune enhancement effect against virus to inhibit viral infection.

Example 4

Immune Enhancement Effect 2 of γ-PGA Against Influenza Virus

In the present example, in order to examine an infection-inhibiting effect of γ-PGA specific to avian influenza virus, the animal's death, virus proliferation, and antibody production in experimental animals infected with influenza virus, were analyzed.

As influenza virus used as a pathogen, H1N1 high pathogenicity influenza virus strain (A/Puerto Rico/8/34(H1N1)) was isolated from a mouse which was donated by Prof. Choi, Young-Ki of microbiological laboratory, College of Medicine, Chungbuk National University to amplify in Madin-Darby canine kidney (MDCK) cells to use, and 6-week-old female Balb/C mice were used as experimental animals.

An animal experiment was carried out as follows.

A control group was administered influenza virus alone, an experimental group 2 was administered γ-PGA twice, and then administered influenza virus, and an experimental group 3 was simultaneously administered γ-PGA and influenza virus.

Influenza virus and γ-PGA were intranasally administered to experimental mice after mice were anesthetized with diethyl ether for 30 minutes, at this time, 30 μl γ-PGA (7,000 kDa) with a final concentration of 0.5% was intranasally administered to each mouse, and $10^4$ $EID_{50}$ (30 μl) of virus was administered.

In the experimental group 3, mice simultaneously administered γ-PGA and influenza virus on the day when the experimental group 2 was infected with virus, were used.

6 mice per group were used in order to measure mortality rate, 18 mice were used in order to measure changes in the amount of virus according to dates, and 15 mice were used as a control group for the experiment, and changes in body weight were monitored on a daily basis in each group to measure weight change rates as a pathogen indicator.

Figure 2:
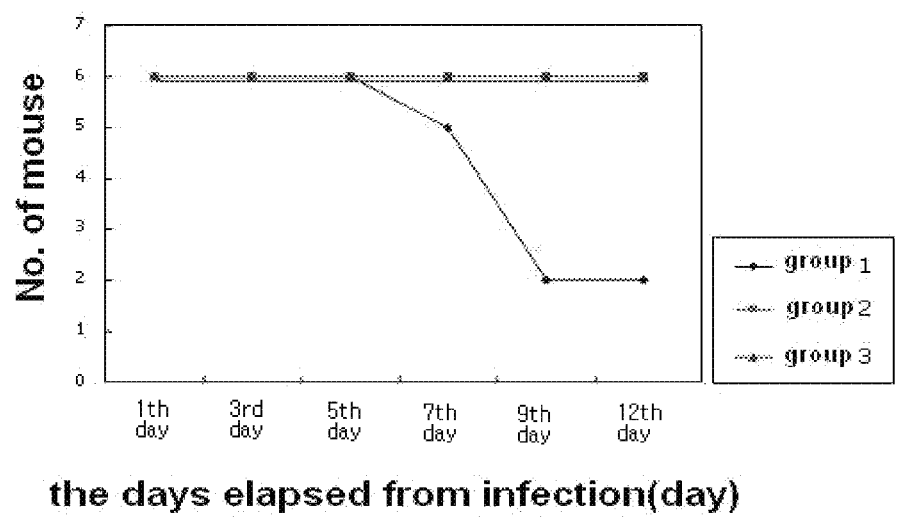
FIG. 2 is a graph showing changes in the number of dead mice according to the days elapsed from infection.
Figure 3:
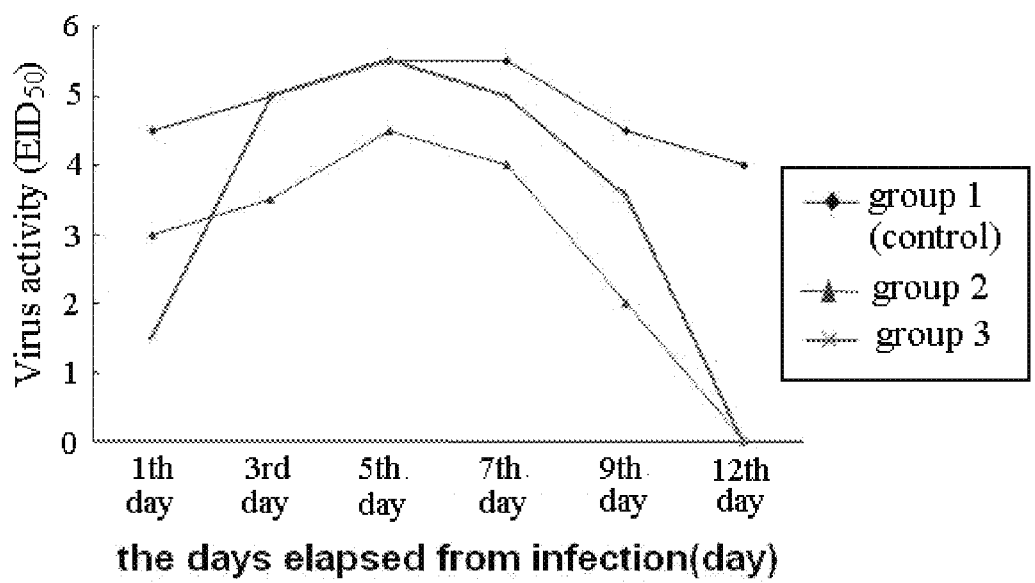
FIG. 3 is a graph showing changes in virus titer in lung tissue of mice infected with virus according to the days elapsed from infection.

As a result, as shown in FIG. 2, in the control group, starting with the death of one mouse 1 week after virus administration, 3 mice died on the 9th day and, on the 12th day, 2 mice with severe pathogenicity remained alive. In the experimental groups 2 and 3, mice only showed mild disease symptoms, and survived more than 12 days after virus administration.

1 week after intranasal administration of virus, 2 mice per group were euthanized at an interval of 2 days (on the 1st day, the 3rd day, the 5th day, the 7th day, the 9th day, and the 12th day after virus administration) to harvest lung tissue and serum of each mouse.

Titers of influenza virus in lung tissue of mice according to dates and each group were measured by HA (Haemagglutination) test as described in Example 2.

Each titer is the value calculated from log 10 dilution of inoculum solution (200 μl). N value is expressed as a logarithmic value ($\log_{10} N = 10^N$). The virus titer showed the maximum value of 5.5 on the 5th day after administering virus in the control group and the experimental group 3.

In the experimental group 2 immunized with γ-PGA before virus administration, the virus titer was relatively low on the first day after virus administration, increased until the 5th day, started to decrease after the 5th day of administration, rapidly decreased after the 7th day of administration, and virus was not detected anymore on the 12th day. In the experimental group 3 simultaneously administered poly-gamma-glutamic acid and virus, the titer was the same as that of the control group on the 5th day after administering virus, but started to decrease after the 5th day of administration, rapidly decreased on the 7th day after virus administration like the experimental group 2, and virus was not detected anymore on the 12th day. This suggests that the administered γ-PGA helps an individual mouse to resist viral infection, and thus is effective for an individual mouse to overcome viral infection due to enhanced immunity.

Figure 4:
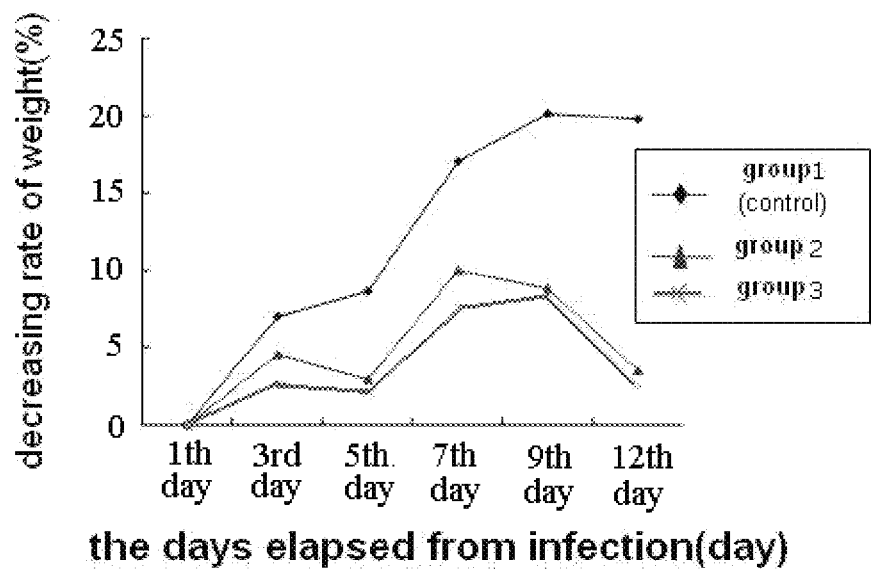
FIG. 4 is a graph showing the weight loss rate of mice infected with virus according to the days elapsed from infection.

In order to measure weight change rates as a pathogen indicator, weight changes were monitored on a daily basis in each group (FIG. 4). Each value is expressed as a percentage of the decreased rate (weight measured after virus administration/weight measured before virus administration).

After virus administration, in the control group, it was observed that the body weight decrease started to increase rapidly after the 5th day of administration, and the mortality rate was more that 20% after the 7th day of administration. In the other two experimental groups, body weight decreased until the 7th day after virus administration, and started to increase after the 7th day of administration and mice recovered, which suggests that there is a correlation between mortality rates and virus titers in lung tissue after virus administration.

From this results, it was confirmed that the poly-gamma-glutamic acid according to the present invention has an immune enhancement effect against influenza virus to inhibit viral infection.

Example 5

Inducement of INF-β Secretion in a Macrophage

The effect of the inventive β-PGA on activation of macrophages, which play an important role in virus inhibitory activity, a primary immune reaction of the immune system, was examined.

As an indicator for macrophage activation, the secretion of interferon beta (INF-β), one of cytokines secreted by macrophages, which mediates innate immune reaction, was examined.

For the examination, RAW 264.7 (ATCC TIB-71), which is a macrophage cell line of Balb/c mouse, was suspended in a DMEM (added with 100 U/ml penicillin-streptomycin, 10% FBS) medium and dispensed into a 6 well plate at a density of $5 \times 10^5$ cells/well to culture in a $CO_2$ incubator for 12 hours, and then, γ-PGA (7,000 kDa) was diluted to concentrations of 0.1% and 0.5% in a DMEM medium containing no FBS, respectively, to culture for 12 hours.

During the culture, culture supernatants of each well were collected at 3, 6, 12, and 12 hours, and the same volume of culture broth as that of the collected culture supernatants, was added again. The amount of secreted INF-β in the collected supernatants was measured by ELISA kit (BD Bioscience, USA).

100 μl standard solution of IFN-β and 100 μl of supernatant were added to a 96 well plate coated with anti-mouse monoclonal antibodies of IFN-β and allowed to react for 1 hour at room temperature, then washed 3 times with wash buffer (250 μl/well), and then 100 μl polyclonal antibodies of each biotinylated anti-mouse INF-β which is a primary antibody, were added and allowed to react for 1 hour at room temperature to wash 3 times with wash buffer (250 μl/well). After that, 100 μl avidin-horseradish peroxidase conjugate which is a secondary antibody, was added and allowed to react for 1 hour at room temperature to wash 3 times, and then allowed to react with a color development reagent, TMB solution for 15 minutes, followed by stopping the color development with 50 μl of stop solution, thus analyzing the amount of each INF-β by measuring at 450 nm by using an ELISA reader.

Figure 5:
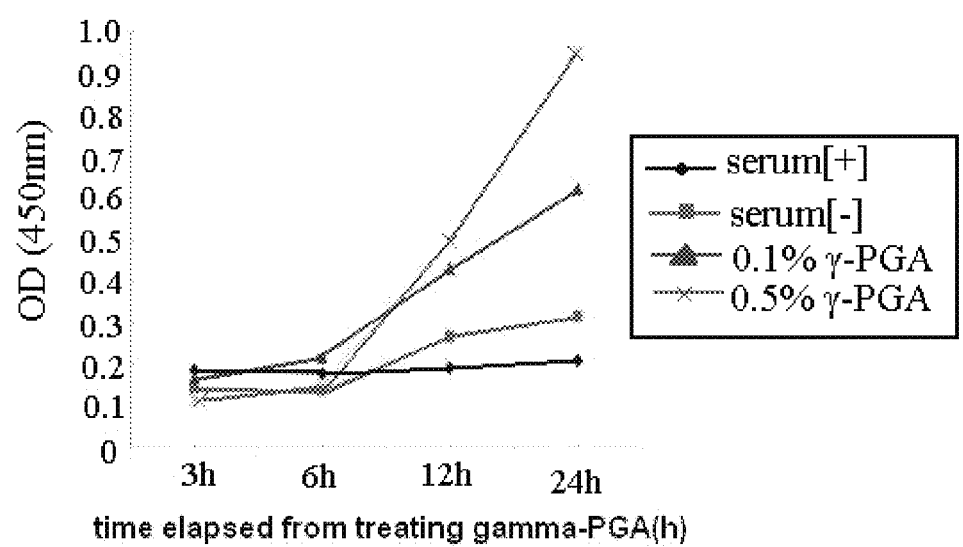
FIG. 5 is a graph illustrating INF-β increase in macrophages by treatment with poly-gamma-glutamic acid.

As a result, as shown in FIG. 5, it was observed that macrophages cultured together with γ-PGA started to secrete interferon beta 6 hours after the culture, and the secreted amount increased with the passage of time. The amount of secreted interferon beta increased as γ-PGA-concentration increased, suggesting that INF-β secretion is γ-PGA-concentration dependent.

It was confirmed that γ-PGA is highly effective to induce macrophage activation, and the macrophage activation is γ-PGA-concentration dependent.

As a result, it was found that γ-PGA according to the present invention induces the secretion of INF-β secreted by macrophages, which is an indicator of the activation of macrophages playing an important role in immune reaction and virus growth inhibition activity.

INDUSTRIAL APPLICABILITY

As described above, the present invention has the effect of providing the composition containing γ-PGA as an effective ingredient, which can be used as an animal feedstuff additive or a pharmaceutical agent for preventing influenza virus infection and various viral diseases as well as a pharmaceutical composition and a functional food to promote human health.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A method of treating diseases caused by virus infection induced by influenza virus comprising administering to a patient in need of such treatment a therapeutically or prophylactically effective dose of a pharmaceutical composition comprising 0.2 to 2.0 parts by weight of poly-gamma-glutamic acid based on 100 parts by weight of the composition, wherein the molecular weight of the poly-gamma-glutamic acid is about 3,000 to about 15,000 kDa.

2. The method according to claim 1, wherein the pharmaceutical composition is a dispersive formulation in which the poly-gamma-glutamic acid is diluted with ethanol.

3. The method of claim 1, wherein the administering comprises preparing a dispersive formulation of the pharmaceutical composition and spraying the patient with the dispersive formulation.

4. The method of claim 1, wherein the administering comprises preparing a food comprising the pharmaceutical composition and feeding the food to the patient.

5. The method according to claim 4, wherein the food is in the form selected from the group consisting of a powder, a granule, a tablet, a capsule, or a drink.

6. The method of claim 1, wherein the administering comprises orally administering the pharmaceutical composition to the patient.

7. A method of treating diseases caused by virus infection induced by influenza virus using a functional food comprising an effective dose of a pharmaceutical composition comprising 0.2 to 2.0 parts by weight of poly-gamma-glutamic acid based on 100 parts by weight of the composition, wherein the molecular weight of the poly-gamma-glutamic acid is about 3,000 to about 15,000 kDa.

8. A method of treating diseases caused by virus infection induced by influenza virus using a feedstuff additive comprising an effective dose of a pharmaceutical composition comprising 0.2 to 2.0 parts by weight of poly-gamma-glutamic acid based on 100 parts by weight of the composition, wherein the molecular weight of the poly-gamma-glutamic acid is about 3,000 to about 15,000 kDa, and wherein the virus is capable of inducing a respiratory infection or systemic infection.

9. The method of claim 2, wherein the concentration of ethanol is in a range from 1% to 50%.

* * * * *